US00PP29527P2

(12) United States Plant Patent
Egger

(10) Patent No.: US PP29,527 P2
(45) **Date of Patent: *Jul. 17, 2018**

(54) ***AGASTACHE* PLANT NAMED 'MORELLO'**

(50) Latin Name: ***Agastache* hybrid**
Varietal Denomination: Morello

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/731,248

(22) Filed: May 9, 2017

(51) Int. Cl.
*A01H 5/02* (2018.01)

(52) U.S. Cl.
USPC ..... Plt./399

(58) Field of Classification Search
USPC ..... Plt./399
See application file for complete search history.

*Primary Examiner* — Susan Beth McCormick Ewoldt
(74) *Attorney, Agent, or Firm* — Klarquist Sparkman, LLP

(57) ABSTRACT

A new and distinct form of *Agastache* plant characterized by red purple flowers in large inflorescences, blooms late spring until frost, a bushy, upright habit, attractive bronze foliage in cool and stress conditions, good winter hardiness, and excellent vigor.

1 Drawing Sheet

Botanical denomination: *Agastache* hybrid.
Variety designation: 'Morello'.

BACKGROUND OF THE INVENTION

The present invention relates to a new and distinct cultivar of *Agastache* hybrid, given the name, 'Morello'. *Agastache* is in the family Lamiaceae. The parents of this new hybrid cultivar include the species *Agastache cusickii, A. cana, and A. pallida*. This new cultivar came out of the planned breeding program to develop new colors and habits in hardy types. The new cultivar is a selection from the cross between the proprietary seedlings 195-3, as the seed parent, and *Agastache* 273-2, as the pollen parent. The new cultivar was selected for its upright habit and branching, hardiness, and large inflorescences of red purple flowers.

Compared to the seed parent, *Agastache* 195-3, the new cultivar is taller and hardier.

Compared to the pollen parent, *Agastache* 273-2, the new cultivar has rose purple flowers rather than pink.

Compared to *Agastache* 'Bolero', an unpatented plant, the new cultivar has more crowns and branching, larger flowers, and larger inflorescences.

This plant exhibits the following characteristics that make it unique:

1. red purple flowers in large inflorescences,
2. blooms late spring until frost,
3. a bushy, upright habit,
4. bronze foliage in cool and stress conditions,
5. good winter hardiness, and
6. excellent vigor.

The new variety has been reproduced only by asexual propagation (stem tip cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a four-month-old plant *Agastache* 'Morello' in bloom grown in a one gallon container in part sun in Canby, Oreg.

FIG. 2 shows a close up of the flowers of the new cultivar.

FIG. 3 shows six-month-old plants in bloom of the new cultivar growing in the field in mid-summer in Canby, Oreg.

DETAILED PLANT DESCRIPTION

The following is a detailed description of the new *Agastache* cultivar based on observations of seven-month-old specimens in early August growing in full sun in the trial field in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form*.—Upright, bushy.
*Type*.—Herbaceous perennial.
*Cold hardiness*.—USDA Zone 5-9.
*Size*.—Grows to 55 cm wide and 82 cm tall to the top of the inflorescences.
*Vigor*.—Excellent.
*Branching*.—About 12 main stems from the base, these branch at every node.
*Stem*.—Square in cross section, grows to 5 mm wide and 45 cm tall to the first flower, pubescent, internodes range from 3 to 8 cm long, Yellow Green 147B.
*Roots*.—White 155B, fibrous, plants root easily from stem tip cuttings.

Leaf:

*Type*.—Simple.

*Arrangement*.—Opposite.

*Shape*.—Ovate, triangular.

*Venation*.—Pinnate.

*Margins*.—Crenate.

*Apex*.—Acute.

*Base*.—Truncate.

*Blade size*.—Grows to 55 mm long and 40 mm wide.

*Surface texture*.—Pubescent on both sides.

*Petiole description*.—22 mm long and 1 mm wide, pubescent, Yellow Green 147B (Greyed Purple N186B when leaves are dark).

*Leaf color*.—Top side Green N137B, vein 147B; bottom side closest to Yellow Green 147B lightly tinted Purple N70A in high light, vein 147B; in cool temperatures or stress the foliage darkens to Brown 200A on top and Purple N70A on bottom side.

*Fragrance*.—Aromatic.

Inflorescence:

*Type*.—Terminal spike with up to 20 whorls.

*Number of flowers*.—Up to 700 per spike.

*Size of inflorescence*.—Grows to 35 cm tall and 6 cm wide.

*Peduncle*.—Grows to 7 cm tall and 2.5 mm wide, pubescent, Yellow Green 147B.

*Pedicel*.—Grows to 2 mm long, pubescent, Greyed Orange 165A.

*Bloom period*.—May through frost in Canby, Oreg.

Flower bud:

*Size*.—20 mm long and 4 mm wide at the widest point prior to opening.

*Description*.—Tubular.

*Surface texture*.—Pubescent.

*Color*.—Red Purple 61A.

Flower:

*Type*.—Zygomorphic.

*Shape*.—Bilabiate, tubular.

*Size*.—32 mm long and 12 mm wide.

*Corolla description*.—30 mm long and spreads to 12 mm wide; both sides Red Purple 71A; glabrous inside and pubescent outside, tube 20 mm long and 1.5 mm to 6 mm wide; 2 upper lobes joined 4 mm long and 5 mm wide, each ovate, tips acute, margin entire; three lower lobes, two spreading sideways and curve out slightly, each 2 mm deep and 3 mm wide, tip obtuse, margin entire; bottom lobe, reflexed, broadly obovate, notched at the tip, margin irregularly incised, 6 mm wide and 4.5 mm deep.

*Calyx description*.—Campanulate, 9 mm long and 2.5 mm wide, pubescent outside and glabrous inside, 5 lobed, lobes ovate, 2 mm long, entire, acuminate, Purple N77A outside, inside Yellow Green 147B on tube to Purple N77B on lobes.

*Pistil description*.—29 mm long, ovary 1 mm long, Yellow Green 147A, style 28 mm long, White NN155B blending to top 4 mm where Purple N78A, stigma two-parted, 1 mm deep, Purple N78A.

*Stamen description*.—4 in number, paired and exerted, top two 9 mm long and bottom two 7 mm long, filaments Purple N78A, anthers 1 mm long, Purple N78B, pollen White 155A.

*Fragrance*.—Aromatic.

*Lastingness*.—A spike blooms for about 4 weeks on the plant.

Fruit/seed: 4 nutlets, 1 mm long, ovoid, Black 202A, low fertility.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

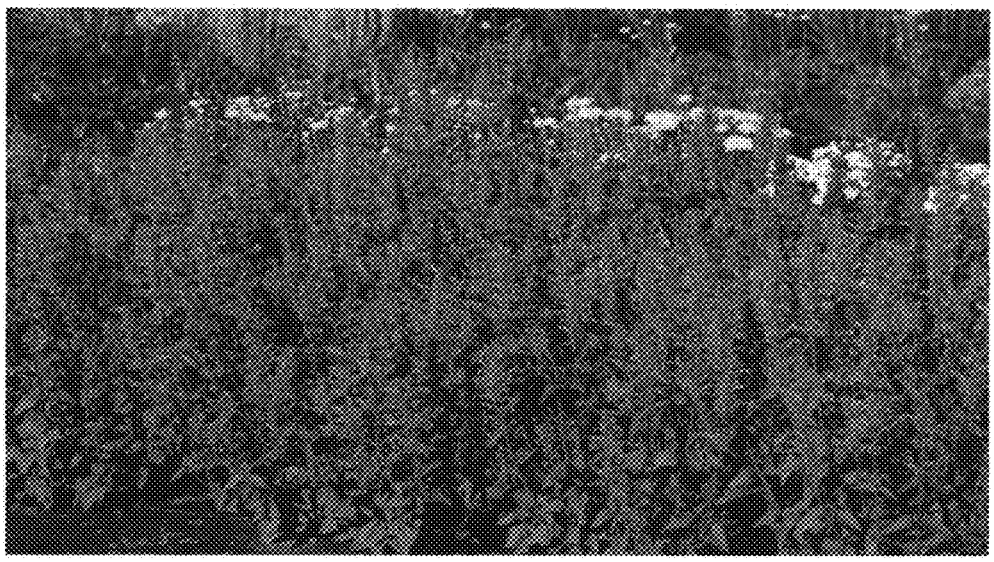

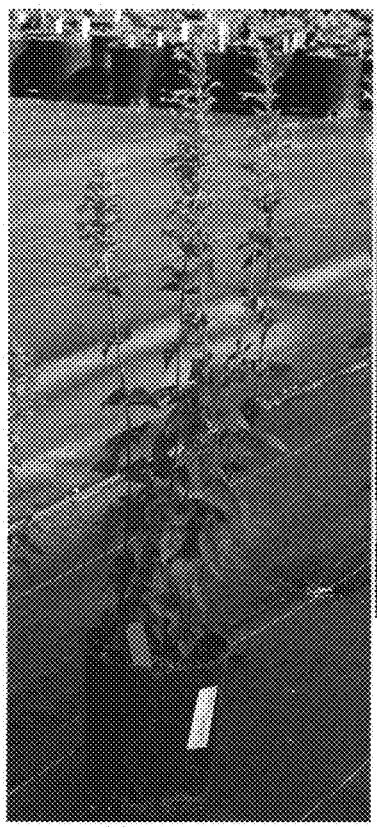
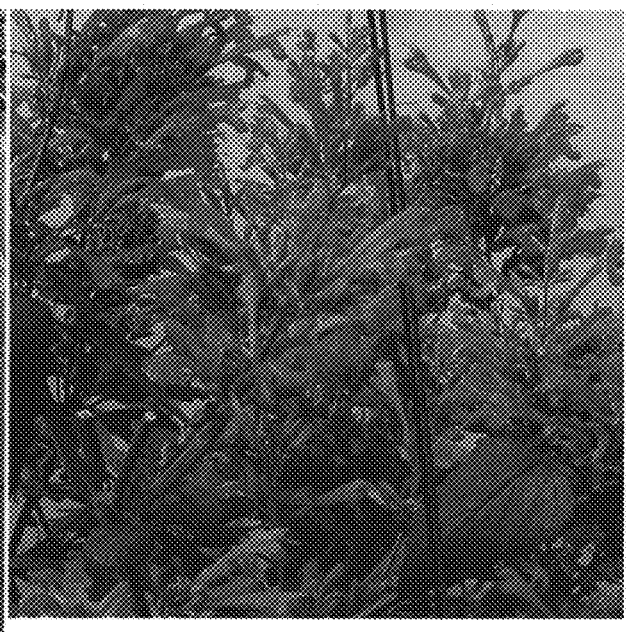
FIG. 1 on left,
FIG. 2 above,
FIG. 3 below.